US012582274B2

(12) United States Patent
Stringer et al.

(10) Patent No.: US 12,582,274 B2
(45) Date of Patent: Mar. 24, 2026

(54) SELF-CLEANING VACUUM CLEANER

(71) Applicant: Dyson Technology Limited, Wiltshire (GB)

(72) Inventors: Robert Matthew Stringer, Swindon (GB); Gemma McLuckie, Poole (GB); Michael Joseph Mathers, Bath (GB); Stefan Koch, Dorset (GB)

(73) Assignee: Dyson Technology Limited, Malmesbury (GB)

( * ) Notice: Subject to any disclaimer, the term of this patent is extended or adjusted under 35 U.S.C. 154(b) by 383 days.

(21) Appl. No.: 18/028,054

(22) PCT Filed: Sep. 22, 2021

(86) PCT No.: PCT/GB2021/052463
§ 371 (c)(1),
(2) Date: Mar. 23, 2023

(87) PCT Pub. No.: WO2022/069872
PCT Pub. Date: Apr. 7, 2022

(65) Prior Publication Data
US 2023/0337875 A1 Oct. 26, 2023

(30) Foreign Application Priority Data

Sep. 30, 2020 (GB) ..................................... 2015464

(51) Int. Cl.
*A47L 9/00* (2006.01)
*A47L 9/14* (2006.01)
(Continued)

(52) U.S. Cl.
CPC ........... *A47L 9/0063* (2013.01); *A47L 9/1409* (2013.01); *A47L 9/20* (2013.01); *A47L 9/2805* (2013.01);
(Continued)

(58) Field of Classification Search
CPC ........ A47L 9/0063; A47L 9/1409; A47L 9/20; A47L 9/2805; A47L 9/2847; A47L 9/2873; A47L 9/2894; A61L 2/084; A61L 2/24
See application file for complete search history.

(56) References Cited

U.S. PATENT DOCUMENTS 6,094,767 A 8/2000 Iimura
8,973,284 B2 3/2015 Shami et al.
(Continued)

FOREIGN PATENT DOCUMENTS

AU 2011265411 A1 7/2012
CN 201870566 U 6/2011
(Continued)

OTHER PUBLICATIONS

CN 103479298 A—English Machine Translation (Year: 2014).*
(Continued)

*Primary Examiner* — Marc Carlson
(74) *Attorney, Agent, or Firm* — Tucker Ellis LLP; Michael G. Craig

(57) ABSTRACT

A docking station is provided for allowing decontaminating parts of a floor care device. The floor care device includes at least one part that is susceptible to contamination when the floor care device is used in a floor care mode. The method may include detecting a transition of the floor care device to a park mode, and in response thereto, executing a decontamination program, the decontamination program including emitting light in a violet portion of the visual spectrum and thereby illuminating the at least one part for the decontamination thereof.

14 Claims, 9 Drawing Sheets

(51) Int. Cl.

| | | |
|---|---|---|
| *A47L 9/20* | (2006.01) |
| *A47L 9/28* | (2006.01) |
| *A61L 2/08* | (2026.01) |
| *A61L 2/084* | (2026.01) |
| *A61L 2/24* | (2006.01) |

(52) U.S. Cl.

CPC ........... *A47L 9/2847* (2013.01); *A47L 9/2873* (2013.01); *A47L 9/2894* (2013.01); *A61L 2/084* (2013.01); *A61L 2/24* (2013.01); *A47L 2201/022* (2013.01); *A47L 2201/028* (2013.01); *A61L 2202/11* (2013.01); *A61L 2202/14* (2013.01)

(56) References Cited

U.S. PATENT DOCUMENTS

| | | | |
|---|---|---|---|
| 10,894,104 B1 | 1/2021 | Kim et al. | |
| 2010/0170104 A1 | 7/2010 | Shami et al. | |
| 2011/0286883 A1 | 11/2011 | Hecht et al. | |
| 2014/0077398 A1 | 3/2014 | Staniforth et al. | |
| 2017/0321877 A1 | 11/2017 | Polidoro | |
| 2019/0167833 A1 | 6/2019 | Yang et al. | |
| 2019/0368180 A1 | 12/2019 | Yaoka et al. | |
| 2020/0000301 A1* | 1/2020 | Morin ................... A47L 9/2805 |
| 2020/0197549 A1 | 6/2020 | Mancinelli et al. | |
| 2020/0298162 A1 | 9/2020 | Jeon et al. | |
| 2020/0298169 A1 | 9/2020 | Jeon et al. | |
| 2021/0031244 A1* | 2/2021 | Jang ................... A47L 11/4091 |
| 2021/0085810 A1* | 3/2021 | Barron ...................... A61L 2/10 |
| 2022/0322904 A1* | 10/2022 | Conrad ................. A47L 9/2873 |
| 2023/0321290 A1* | 10/2023 | McLuckie ................. F24F 8/90 250/432 R |
| 2023/0330285 A1* | 10/2023 | McLuckie ................. A61L 2/10 |
| 2023/0330293 A1* | 10/2023 | Stringer ................... A47L 9/20 |
| 2023/0337875 A1* | 10/2023 | Stringer ............... A47L 9/2894 |

FOREIGN PATENT DOCUMENTS

| | | | | | |
|---|---|---|---|---|---|
| CN | 103479296 A | | 1/2014 | |
| CN | 103479298 A | * | 1/2014 | |
| CN | 103480015 A | | 1/2014 | |
| CN | 209982181 U | | 1/2020 | |
| CN | 111380180 A | | 7/2020 | |
| DE | 4206190 A1 | | 5/1993 | |
| EP | 2468167 A2 | * | 6/2012 | ............... A47L 5/26 |
| EP | 3575503 A1 | | 12/2019 | |
| EP | 3712520 A1 | | 9/2020 | |
| EP | 3712521 A1 | | 9/2020 | |
| EP | 3771395 A1 | | 2/2021 | |
| GB | 2500011 A | | 9/2013 | |
| JP | 2005-040351 A | | 2/2005 | |
| JP | 2005-040352 A | | 2/2005 | |
| JP | 2005-124861 A | | 5/2005 | |
| JP | 2006-274573 A | | 10/2006 | |
| JP | 2010-227466 A | | 10/2010 | |
| JP | 2010-268941 A | | 12/2010 | |
| JP | 2012-245218 A | | 12/2012 | |
| KR | 10-2006-0027207 A | | 3/2006 | |
| KR | 20060027207 A | * | 3/2006 | |
| KR | 10-2010-0090549 A | | 8/2010 | |
| KR | 10-2011-0042990 A | | 4/2011 | |
| KR | 10-1110302 B1 | | 2/2012 | |
| KR | 10-1185270 B1 | | 9/2012 | |
| KR | 10-2014-0047432 A | | 4/2014 | |
| KR | 20140047432 A | * | 4/2014 | |
| KR | 10-2015-0006525 A | | 1/2015 | |
| KR | 10-1507922 B1 | | 4/2015 | |
| KR | 10-2017-0049041 A | | 5/2017 | |
| KR | 10-1897245 B1 | | 9/2018 | |
| KR | 10-2035556 B1 | | 10/2019 | |
| KR | 10-2020-0033117 A | | 3/2020 | |
| KR | 10-2020-0084157 A | | 7/2020 | |
| KR | 20220122003 A | * | 9/2022 | ......... H01L 25/0753 |
| WO | 2005/074776 A1 | | 8/2005 | |
| WO | 2022/069869 A1 | | 4/2022 | |

OTHER PUBLICATIONS

Examination Report received for GB Application No. 2015466.2, mailed on Jan. 25, 2023, 1 page.

Examination Report received for GB Application No. 2015466.2, mailed on May 15, 2023, 2 pages.

Search Report received for GB Application No. 2015464.7, mailed on Mar. 24, 2021, 1 page.

Search Report received for GB Application No. 2015466.2, mailed on Feb. 19, 2021, 2 pages.

Search Report received for GB Application No. 2015468.8, mailed on Mar. 15, 2021, 2 pages.

Search Report received for GB Patent Application No. 2015463.9, mailed on Mar. 23, 2021, 1 page.

International Search Report and Written Opinion received for PCT Patent Application No. PCT/GB2021/052438, mailed on Nov. 29, 2021, 8 pages.

International Search Report and Written Opinion received for PCT Patent Application No. PCT/GB2021/052462, mailed on Dec. 23, 2021, 8 pages.

International Search Report and Written Opinion received for PCT Patent Application No. PCT/GB2021/052463, mailed on Jan. 5, 2022, 8 pages.

International Search Report and Written Opinion received for PCT Patent Application No. PCT/GB2021/052464, mailed on Dec. 14, 2021, 9 pages.

International Search Report and Written Opinion received for PCT Patent Application No. PCT/GB2021/052465, mailed on Jan. 5, 2022, 10 pages.

* cited by examiner

SELF-CLEANING VACUUM CLEANER

RELATED APPLICATION DATA

This application is the National Stage of International Application No. PCT/GB2021/052463 filed Sep. 22, 2021, and claims benefit of United Kingdom Application No. 2015464.7 filed Sep. 30, 2020, each of which are herein incorporated by reference in their entirety.

TECHNICAL FIELD

The present invention relates to a docking station for a floor care device. The present invention further relates to a combination of a docking station and a floor care device.

BACKGROUND

Floor care devices come in many different types. Vacuum cleaners use pressure differentials to suck dust and other small and loose dirt from floors and other surfaces. Other floor care devices use water, possibly in combination with soap or other cleansing agents to clean floor surfaces. Also, a large variety of vacuum cleaners exist. Some vacuum cleaners use vacuum cleaner bags for filtering the dirt out of the generated air stream and collecting it therein. Other vacuum cleaners may, e.g., use cyclonic filters for filtering out the dirt. Traditional canister vacuum cleaners are now often replaced by newer models like, e.g., cordless stick vacuums, corded upright vacuum cleaners and robotic vacuum cleaners. For smaller cleaning tasks, compact handheld vacuum cleaners are used, which although typically used on a variety of surfaces, are to be considered floor care devices too.

Because floor care devices are used in dirty places and come into contact with dirty surfaces, they pick up a lot of contamination, not all of which ends up in the reservoirs that are provided for that purpose. In addition to visible contamination, the floor care devices pick up bacteria and other microbes too. In particular device parts that come in direct contact with the surfaces to be cleaned or that are regularly touched and held by the user can gather a lot of such microbes. This microbial contamination may form a health risk for the user. Vacuum cleaner filters may pick up microbial contamination too. When the microbes gathering and growing on the filter surfaces are later released into the surroundings or touched by the user when cleaning or replacing the filter, this may lead to similar risks.

As a consequence, there is a need for ways to better protect the users of vacuum cleaners against contact with unwanted microbes while cleaning their homes and offices.

SUMMARY OF THE INVENTION

According to a first aspect of the invention, a docking station for a floor care device is provided. The floor care device comprises at least one part that is susceptible to contamination when the floor care device is used in a floor care mode. The docking station comprises a docking bay for receiving and holding at least an element of the floor care device, a docking sensor for providing a docking signal when at least the element of the floor care device is held in the docking bay, at least one light source for emitting light in a violet portion of the visual spectrum and a docking station controller. The at least one light source is arranged in such a way as to illuminate the at least one part of the floor care device by emitting the light while the floor care device is being held in the docking bay. The docking station controller is operatively coupled to the docking sensor and the at least one light source and operative to receive the docking signal and to execute, in response thereto, a decontamination program. The decontamination program includes using the at least one light source to illuminate the at least one part of the floor care device for the decontamination thereof.

Docking stations are typically provided for cordless floor care devices that need to be charged in between cleaning sessions but may also be used for parking corded floor care devices. Decontaminating parts of the floor care device while being docked brings the advantage that the decontamination does not use any battery power that could otherwise have been used for using the floor care device for cleaning floors. The amount of time needed for fully decontaminating the contaminated parts will generally be of the same order as the time needed for charging the batteries of the floor care device. When, e.g., using low intensity 405 nm LED light, illumination times of 30 minutes to a few hours may be needed for getting rid of most of the microbes. This decontamination process can thus be performed while the floor care device is out of operation anyhow. Furthermore, by integrating the light source in the docking station and decontaminating the parts when the floor care device is docked, it is ensured that the decontamination process does not drain the floor care device's batteries. Yet another advantage is that this functionality can easily be added to an existing floor care system by only replacing or upgrading the docking station, and without having to replace the whole floor care device.

In an embodiment, the docking station further comprises a contamination detector for detecting contamination on a contaminated portion of the at least one part of the floor care device and the decontamination program comprises selectively illuminating the contaminated portion. Since visually contaminated portions may provide relatively good conditions for the microbes to adhere to the device, selectively illuminating such visibly contaminated parts may improve the decontamination process. The contamination detection may use an optical sensor measuring the reflectance of light of a particular wavelength at a surface of the at least one part. The light used for this reflection measurement may be the light from the at least one light source but may also be provided by a separate light source, possibly emitting light at a different wavelength.

Preferably, the docking station comprises a communication unit, operatively coupled to the docking station controller, for enabling communication between the docking station controller and a floor care controller of the floor care device. Such a communication unit may, e.g., be used for receiving information from various sensors of the floor care device, or for receiving specific instructions from a controller of the floor care device. Further, the communication unit may send similar sensor signals and/or instructions to the controller of the floor care device.

In an exemplary embodiment, the decontamination program comprises receiving, from the floor care controller, a contamination signal indicating a contaminated portion of the at least one part, and in response to the contamination signal selectively illuminating the contaminated portion. Sensors positioned on and in the floor care device may be better positioned to detect the contamination on some parts of the floor care device, than external sensors positioned on the docking station. Of course, a combination of external and internal sensors may be used for optimal contamination detection. Because decontamination with violet visible light does not require a direct line of sight, the use of only external light sources located at the docking station may be enough to illuminate all relevant parts of the floor care device. However, additional light sources may be strategically positioned in and on the floor care device too.

As a further example, the decontamination program may comprise sending, to the floor care controller, an instruction to rotate the at least one part, and illuminating the at least one part during and/or after rotating the at least one part. This will ensure that all sides of the rotatable part will be sufficiently illuminated for optimal decontamination.

According to one more aspect of the invention, a combination is provided of one of the docking stations and one of the floor care devices described above. As indicated before, the light source and the control thereof may be located in the docking station, in the floor care device or in a combination of both.

In a special combination, the floor care device further comprises at least a second part that is susceptible to contamination when the floor care device is used in the floor care mode. When the floor care device is received in and held by the docking bay, the at least one part is situated between the at least one light source and the second part and configured to guide the light emitted by the light source towards the second part. For example, the light source on the docking station may illuminate a dust bin of the floor care device and the dust bin serves as a light guide for illuminating a shroud or air filter of the floor care device.

Preferably, the floor care device comprises a floor care controller, and the docking station and the floor care device each comprise a communication unit, operatively coupled to their respective controllers for enabling communication between the docking station controller and a floor care controller of the floor care device. This communication may, e.g., be used for exchanging sensor signals or control instructions between the docking station and the floor care device. Such sensor signals may, e.g., comprise a contamination signal indicating a contaminated portion of the at least one part. The communicated control instructions may, e.g., include an instruction to rotate a rotatable part or an instruction to operate a light source.

According to a further aspect there is provided a method of decontaminating a floor care device, the floor care device comprising at least one part that is susceptible to contamination when the floor care device is used in a floor care mode, the method comprising, detecting a transition of the floor care device to a park mode and, in response thereto, executing a decontamination program, the decontamination program including emitting light in a violet portion of the visual spectrum and thereby illuminating the at least one part for the decontamination thereof.

The violet portion of the visual spectrum is typically defined as spanning the range of about 380 to 450 nm. The light used may thus, e.g., have a wavelength of about 405 nm. Light of these wavelengths is known to be very effective in killing any microbes that may have accumulated on the illuminated surfaces. Although such light is known to be used in light fixtures used for cleaning rooms in hospitals and in standalone curing lights used for 3D printer resin and nail polish, it has so far not been used in floor care devices or for cleaning contaminated parts of floor care devices. The use of violet visible light for this particular implementation brings a number of advantages that are not found in UV or near UV light. For example, the low energy visible light does not damage the material of the surfaces it illuminates. This is especially advantageous because most floor care devices are at least partially made of plastics that are easily damaged by UV light. In addition thereto, the visibility of the light makes it clear to the user and other bystanders when the device is operating in a cleaning mode. Another important advantage of the violet visible light is that no direct line of sight between the light source and the surface or part to be cleaned is needed. Indirect irradiation of the violet visible light helps to get rid of the microbial contamination too.

It is to be noted that emitting light in a violet portion of the visual spectrum as part of a decontamination process means that the emitted light contains a significant portion of light in that part of the electromagnetic spectrum and that the intensity of that significant portion is sufficient to have a useful anti-microbial and decontaminating effect. The emitted light does not need to be exclusively in the violet portion of the visual spectrum. As long as there is a sufficient intensity of light in that portion of the spectrum, and preferably at or around the 405 nm wavelength, for achieving a decontaminating effect, light of other parts of the electromagnetic spectrum may be emitted too. Further it is noted that, as part of the decontamination process, the intensity of the emitted light may vary over time. Such variations may be gradual and continuous or in the form of a pattern of light pulses. If pulsed light is used, the frequency, duration and intensity of the pulses may either be constant or varying.

The emitted light is preferably used for at least illuminating those parts of the floor care device that tend to attract a lot of microbial contamination or that have a larger probability of passing on such contamination to its users. Because some parts of a floor care device, e.g. the brush bar in a cleaner head, rotate during use, a stationary light source may not be able to illuminate the full part at once. Thus, in a preferred embodiment, the at least one part is a rotatable part, and the decontamination program further comprises illuminating the at least one part during and/or after rotating the rotatable part. This will ensure that all sides of the rotatable part will be sufficiently illuminated for optimal decontamination.

The decontamination program further comprises detecting contamination on a contaminated portion of the at least one part and selectively illuminating the contaminated portion. Since visually contaminated portions may provide relatively good conditions for the microbes to adhere to the device, selectively illuminating such visibly contaminated parts may improve the decontamination process. The contamination detection may use an optical sensor measuring the reflectance of light of a particular wavelength at a surface of the at least one part. The light used for this reflection measurement may be the light from the at least one light source but may also be provided by a separate light source, possibly emitting light at a different wavelength.

According to a further aspect, a floor care device is provided, which is configured to operate in a floor care mode and a park mode, the floor care device comprising at least one part that is susceptible to contamination when the floor care device is used in the floor care mode, at least one light source for emitting light in a violet portion of the visual spectrum, the at least one light source being arranged in such a way as to illuminate the at least one part when emitting the light, and a floor care controller, operatively coupled to the at least one light source and operative to detect a transition of the floor care device to the park mode and, in response thereto, to execute a decontamination program, the decontamination program including using the at least one light source to illuminate the at least one part for the decontamination thereof. While the use of violet visible light is found to be an effective way to eliminate microbial contamination, it is a time-consuming process. When, e.g., using low intensity 405 nm LED light, illumination times of 30 minutes to a few hours may be needed for getting rid of most of the microbes. While in the floor care mode, the use of the floor care device will lead to faster contamination than the light source can prevent. Decontaminating during use may therefore not be very useful or energy efficient. However, when the floor care device switches to the park mode, e.g., by turning off its active floor cleaning parts and/or when connecting to a charger for charging a battery pack of the floor care device, the light source is turned on and the decontamination program can start.

The at least one part comprises a user contact area, specifically designed for being contacted by a user during normal use of the floor care device. Such parts may, e.g., include a handle for holding the floor care device during use in the floor care mode or a button, a knob, a lever or a touch screen provided for user interaction with the floor care device. Because the user needs to touch these parts during use, the user contact areas tend to attract a lot of microbial contamination and have a larger probability of passing on such contamination to the users. When decontaminating those parts while the floor care device is in the park mode, it is ensured that they will be clean when the user picks up the device for the subsequent cleaning session.

Other useful parts to decontaminate are an air filter, a dust bin, or a shroud for at least partially enclosing the dust bin. Such parts tend to attract a lot of microbial contamination because they are designed to come into contact with the dirt that has been sucked up from the floor. The dust bin is often removable and/or can be opened to allow the collected dust to be dispensed with. During the emptying of the dust bin, it is likely that the shroud is touched by the user and comes into contact with the collected dirt.

The floor care device further comprises at least a second part that is susceptible to contamination when the floor care device is used in the floor care mode, and wherein the at least one part is arranged between the at least one light source and the second part and configured to guide the light emitted by the light source towards the second part. For example, the at least one part is a dust bin. The dust bin is often made of a transparent or-semi-transparent material to allow the user to observe its filling level. This transparency makes the dust bin very suitable for acting as a light guide for the violet visible light emitted by the light source. Via the dust bin, the light may, e.g., be guided to an air filter, or a shroud for at least partially enclosing the dust bin.

When the at least one part is a rotatable part, such as a fan or a brush bar, the floor care device may further comprise a rotation unit for rotating the rotatable part, and the decontamination program may further comprise illuminating the rotatable part during and/or after rotating the rotatable part. This will ensure that all sides of the rotatable part will be sufficiently illuminated for optimal decontamination.

As a further option, the floor care device may comprise a contamination detector for detecting contamination on a contaminated portion of the at least one part and the decontamination program may comprise selectively illuminating the contaminated portion. Since visually contaminated portions may provide relatively good conditions for the microbes to adhere to the device, selectively illuminating such visibly contaminated parts may improve the decontamination process. The contamination detection may use an optical sensor measuring the reflectance of light of a particular wavelength at a surface of the at least one part. The light used for this reflection measurement may be the light from the at least one light source, but may also be provided by a separate light source, possibly emitting light at a different wavelength.

BRIEF DESCRIPTION OF THE DRAWINGS

Embodiments of the invention will now be described by way of example with reference to the accompanying drawings, in which.

DETAILED DESCRIPTION

Figure 1:
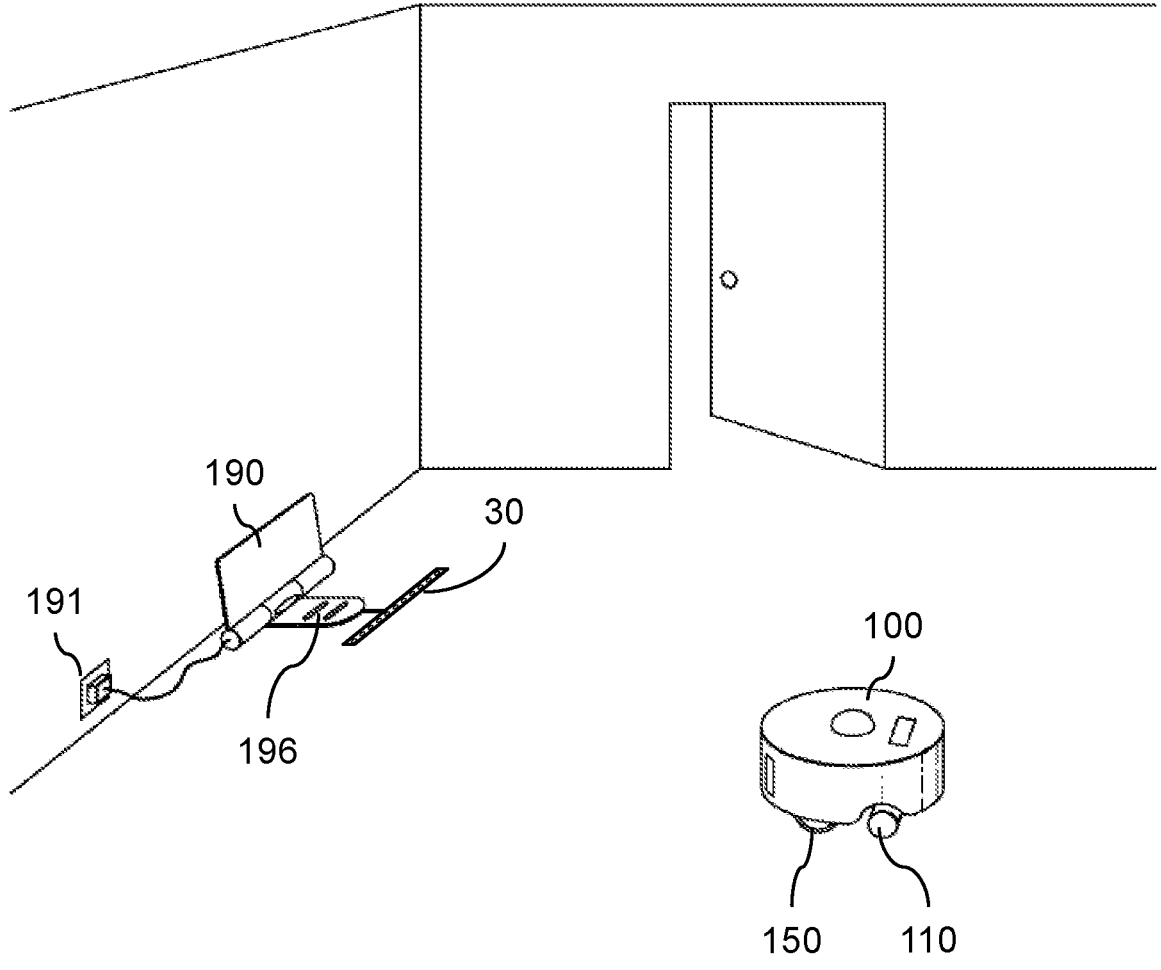
FIG. 1 shows a robotic vacuum cleaner and a docking station for this vacuum cleaner.

FIG. 1 shows a robotic vacuum 100 cleaner and a docking station 190 for this vacuum cleaner 100. When in a floor care mode, the battery powered robotic vacuum cleaner 100 finds its own way through the room, while vacuum cleaning the floor surface on which it travels. Wheels or tracks 150 of the vacuum cleaner 100 are controlled by a controller to make sure that all of the floor area to be cleaned is visited. While traveling through the room, a rotating brush bar 110 sweeps dirt and dust up from the floor and a fan inside the vacuum cleaner 100 sucks up the swept-up dirt and dust that is then stored in a dust bin. When instructed by the user, when the floor care job is done, or when the vacuum cleaner batteries run out of power, the robotic vacuum cleaner 100 returns to the docking station 190. The docking station 190 is connected to a power socket 191 in the wall, which provides for the power needed to recharge the batteries of the vacuum cleaner 100. Contact points 196 are provided on the docking station 190 for connecting to complementary contact point underneath the robotic vacuum cleaner 100. These contact points 196 can serve multiple purposes, such as charging the vacuum cleaner batteries, detecting the docking of the vacuum cleaner 100 in the docking station 190 and communicating sensor and control signals between controllers of the two devices.

While travelling through the room and picking up dirt and dust, the vacuum cleaner 100 may pick up harmful bacteria and other microbes too. Especially the brush bar 110 and the wheels 150, which are in constant contact with the dirty floor, are susceptible to such unwanted contamination. However, such microbial contamination can, e.g., also be collected by parts of the vacuum cleaner chassis that bump into furniture and other objects, or by filters and the dust bin, that get into contact with the swept-up dirt and dust.

To reduce the risk of a user coming into contact with these microbes, or the microbes being scattered around the house during subsequent cleaning trips, the docking station 190 comprises a light source 30 that can emit visible light in the violet portion of the visual spectrum. The violet portion of the visual spectrum is typically defined as spanning the range of about 380 to 450 nm. The light used may thus, e.g., have a wavelength of about 405 nm. Light of these wavelengths is known to be very effective in killing any microbes that may have accumulated on the illuminated surfaces. When the robotic vacuum cleaner 100 is parked in the docking station 190, the contact points 196 detect the presence of the vacuum cleaner 100 and a decontamination program may be started. The light strip 30 shown in FIG. 1 is part of and powered by the docking station 190 and positioned to illuminate the brush bar 110 of the vacuum cleaner 100, when docked. In order to make sure that not just a portion of the brush bar 110 is properly decontaminated, the controller of the docking station 190 may instruct the controller of the vacuum cleaner 100 to rotate the brush bar 110 during the decontamination program. Additional or alternative light sources may be provided at the docking station 190 or the vacuum cleaner 100 for illuminating other parts of the vacuum cleaner 100.

Figure 2:
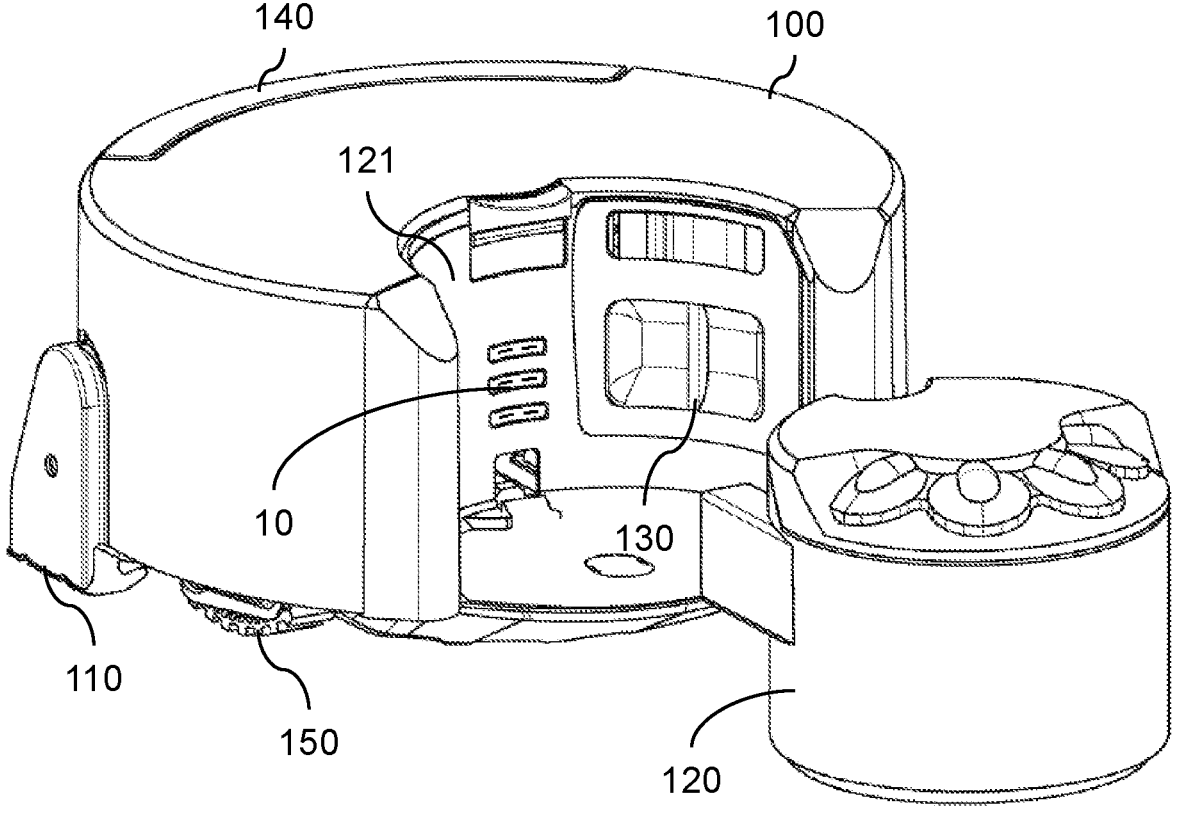
FIG. 2 shows the robotic vacuum cleaner of FIG. 1 in more detail and with its dust bin removed.

FIG. 2 shows the robotic vacuum cleaner 100 of FIG. 1 in more detail and with its dust bin 120 removed. In many robotic and non-robotic vacuum cleaners, a dust bin 120 collects all the dust and is emptied by the user after being detached from the rest of the device 100. The act of emptying of the dust bin 120 forms a health and safety risk, both by transferring microbes from the dust bin to the user and vice versa. To decontaminate the dust bin 120, the vacuum cleaner of FIG. 2 therefore comprises an array of violet LEDs 10, which are integrated in the shroud 121 for the dust bin 120, can illuminate the dust bin 120 as part of the decontamination program. Since the dust bin 120 is typically made of at least partially transparent material to allow the user to observe its filling level, the bin walls may function as a light guide. The light guide function of the dust bin 120 may not just ensure that the whole dust bin 120 is decontaminated, but also the other parts of the vacuum cleaner 100, located close thereto. For example, an air filter 130, located at an outlet of the dust bin 120 may be illuminated by the LED array 10, via the light guiding dust bin wall.

Figure 3:
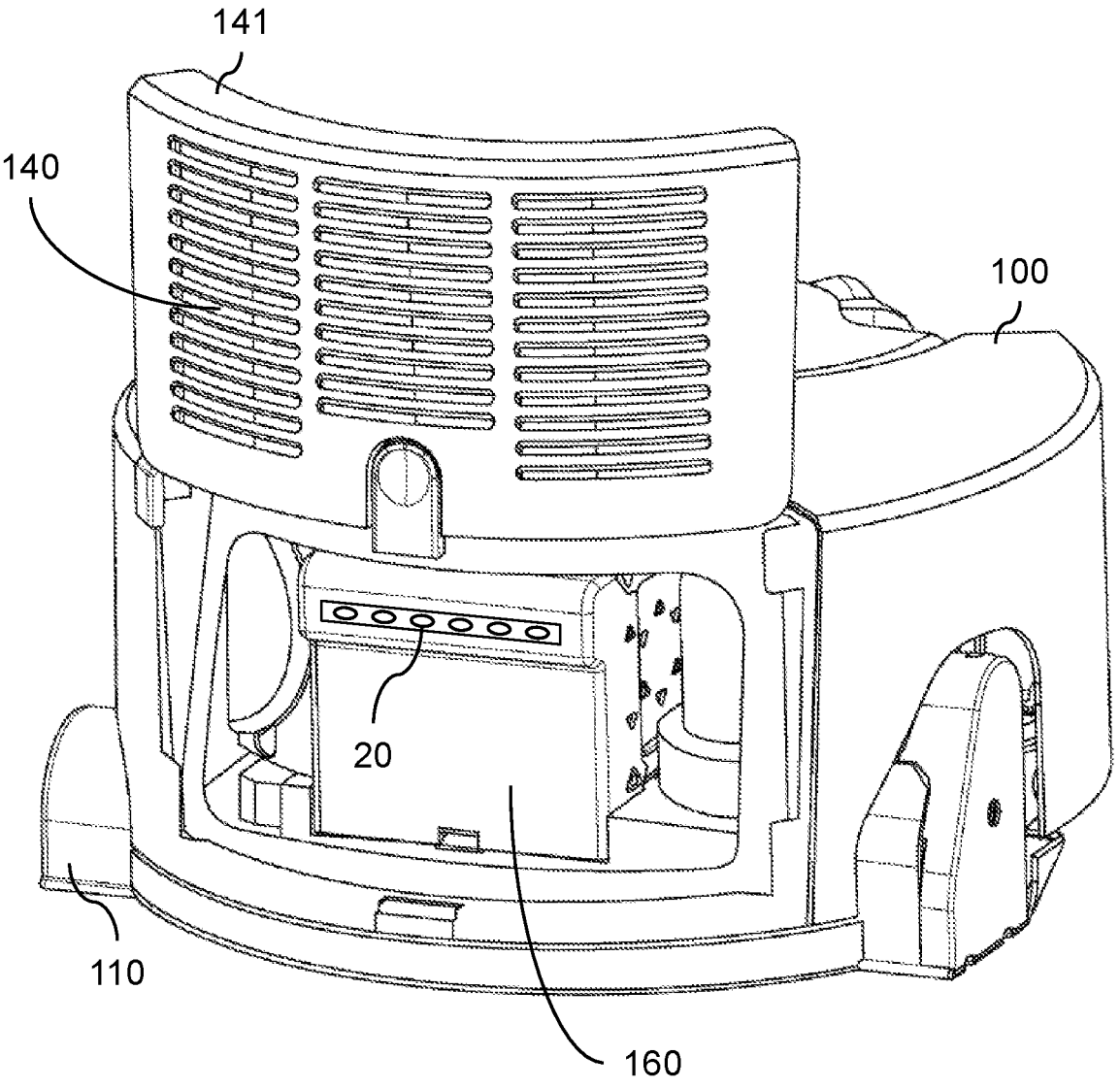
FIG. 3 shows the robotic vacuum cleaner of FIGS. 1 and 2 from a different viewpoint.

FIG. 3 shows the robotic vacuum cleaner 100 of FIGS. 1 and 2 from a different viewpoint. An outlet filter 140 is integrated in a sliding door 141, that is opened to show the interior of the robotic vacuum cleaner 100. With the sliding door 141 opened, it is possible to, e.g., replace the battery pack 160, or to take out the outlet filter 140, such that it can be cleaned or replaced. An LED strip 20 (again violet visible light, e.g. 405 nm) is located inside the vacuum cleaner 100 to illuminate and thereby decontaminate the outlet filter 140 when the sliding door 141 is closed and the decontamination program is running. Additionally, because the decontamination process does not require a direct line of sight from the light source, the LED strip 20 may help to decontaminate other parts in the interior of the vacuum cleaner, such as the battery pack 160. If this side of the vacuum cleaner 100 is positioned opposite a rear wall of the docking station 190 while the decontamination program is executed, the emitted light may further illuminate, and thus contaminate, a rear wall of the docking station 190. However, the filter 140 may partially block the light coming through the openings in the sliding door 141, which may negatively affect its decontaminating power.

Figure 4:
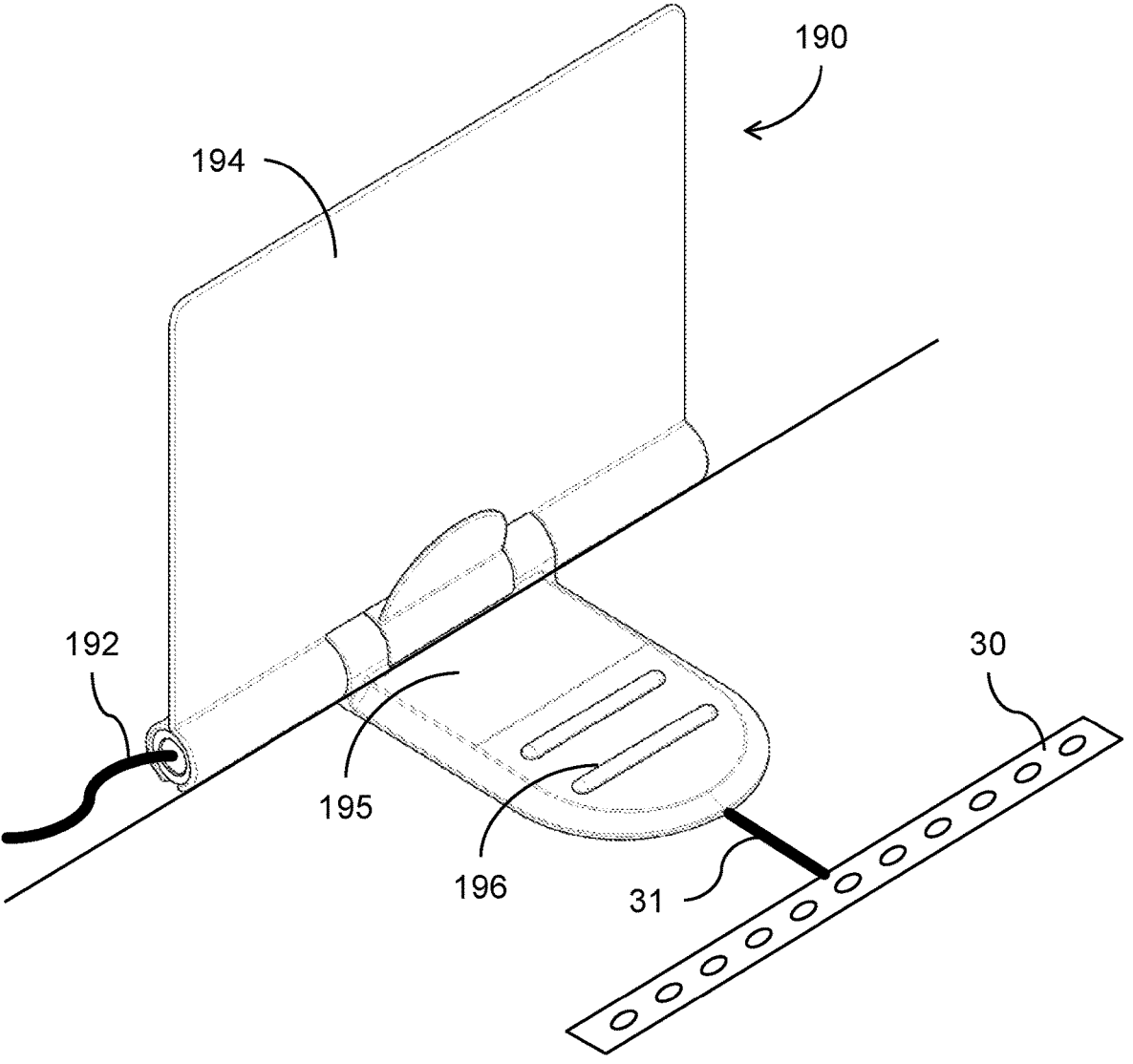
FIG. 4 shows the docking station of FIG. 1 in more detail.

FIG. 4 shows the docking station 190 of FIG. 1 in more detail. A power cable 192 connects the docking station to the power socket 191 in the wall. A rear wall 194 may show a known colour or pattern which can serve as a visual indication that allows the robotic vacuum cleaner 100 to recognise the docking station 190 and to move itself into the docked position. When in the docked position, contact points 196 establish an electrical connection between the docking station 190 and the vacuum cleaner 100. This electrical connection is used for detecting the docking of the vacuum cleaner 100, charging its batteries and/or communicating sensor and control signals between the controllers of the docking station 190 and the vacuum cleaner 100. The contact points 96 are integrated in a foot 195 of the docking station 190, which may further comprise additional electronics, such as the docking station controller. Alternatively, the controller is hidden behind the rear wall 194.

A power line 30 provides power to the LED strip 30, which is provided for emitting the decontaminating violet visible light. The LED strip 30 is positioned such that, when the robotic vacuum cleaner 100 is docked in the docking station, the brush bar 110 is positioned just above the LED strip 30. Because the LED strip 30 will illuminate the underside of the brush bar 110, the decontamination program may comprise rotating the brush bar 110 such that all sides are illuminated equally. This rotation of the brush bar 110 may be realised by the controller of the vacuum cleaner 100, in response to a signal from the controller of the docking station 190. The rotation may take place continuously or in steps, while the decontamination program is running.

In a very basic implementation, the LED strip 30 can only be switched on and off. The decontamination program may then just involve switching the LED strip 30 on for a predetermined amount of time, e.g., 45 minutes or one and a half hour, or keeping it on for as long as the batteries of the vacuum cleaner 100 are charging. In a special implementation, the LED strip 30 comprises an array of contamination detectors that can detect which parts of the brush bar 110 are most heavily contaminated. Contamination detection may, e.g., be realised by measuring how the light from the LED strip 30 is reflected by the brush bar 110. The docking station controller may then decide to selectively illuminate only (or predominantly) the contaminated parts. For best results, this may be combined with rotating the brush bar 110 in order to detect and selectively illuminate those parts that have the highest risk of containing microbial contamination.

It should be clear that the LED strip 30 of the docking station, the LED array 10 in the shroud 121 and the LED strip 20 behind the outlet filter 140 are just a few examples of the light sources that may be installed for decontaminating the robotic vacuum cleaner 100, while docked. The light sources may only be provided in the docking station 190 or only in the vacuum cleaner. However, preferably, as discussed above, the decontamination program uses a combination of both in order to be able to decontaminate all relevant parts in the most efficient and effective way. Control of the decontamination process may be performed by the controller in the docking station 190, by the controller in the vacuum cleaner 100, or by a combination of both.

Figure 5:
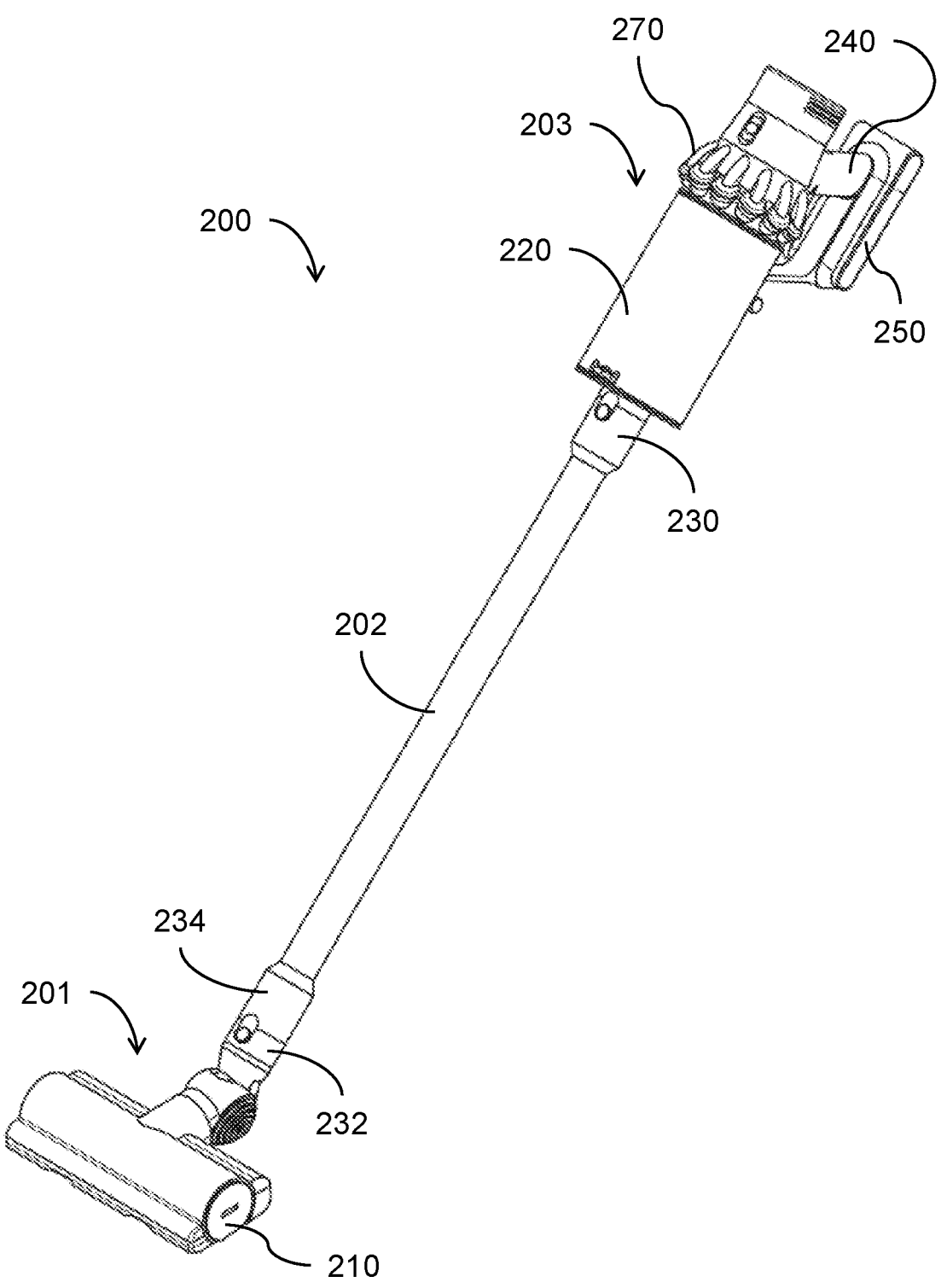
FIG. 5 shows a stick vacuum cleaner.

FIG. 5 shows a stick vacuum cleaner 200, wherein the current invention may be advantageously used. Stick vacuum cleaners 200 are operated by the user. In addition to the easily contaminated parts already seen in the robotic vacuum cleaner 100, i.e., a brush bar 210, a dust bin 220 and various filters, a stick vacuum cleaner comprises many parts that are frequently touched by the user. For example, there is a handle 240 which is held by the user during use of the vacuum cleaner 200. The cleaner head 201 comprises a stick connector 232 for connecting to a cleaner head connector 234 of the stick 202. Different types of cleaner heads 201 may be used for different types of floor surfaces. When replacing cleaner heads 201, the user will touch and hold the connectors, which may lead to microbial contamination. Similarly, the other end of the stick 202 comprises a body connector 230 for connecting the stick to the main body 203. When replacing the stick 202 and cleaner head 201 with a shorter attachment piece, for example for cleaning furniture or curtains, the user will touch and hold the body connector 230. Strategically positioned light sources, e.g. on the battery pack 250, under the dust bin 220 or on the cleaner head 201 may be used for illuminating such often touched parts of the vacuum cleaner 200 in order to reduce the risk of bringing users into contact with harmful microbes.

The stick vacuum cleaner 200 is powered by the battery pack 250. Charging the battery pack may be done by simply connecting a power cable to a charger circuit of the vacuum cleaner 200. When a connection with the power cable is detected, the controller of the vacuum cleaner 200, preferably housed in the main body 203, switches to a park mode. In the park mode, the controller controls the charging of the battery pack 250 as well as the decontamination of possibly contaminated parts. Alternatively, the vacuum cleaner 200 may switch to the park mode and start a decontamination program automatically when it has not been used for vacuum cleaning for a predetermined amount of time, e.g. 10 minutes. If the battery pack 250 is not being charged, starting the decontamination program may depend on the current state of charge of the battery pack 250. For example, the decontamination program may only start when the battery pack 250 is still charged to at least 50% of its capacity. Optionally, a smaller power saving decontamination program may be started in dependence of the current charging state of the battery pack 250. When it is detected that a partially depleted battery pack 250 has just been replaced by a fresh and fully charged one, this may also trigger the start of a decontamination program, possibly after a short delay to ensure that the user is not going to use the vacuum cleaner 200 for cleaning.

As will be illustrated by the examples provided below, the light source for realising the decontamination may be part of the vacuum cleaner 200. Alternatively (or additionally), the vacuum cleaner 200 is placed in a docking station when not being used for cleaning. The docking station can provide a practical way of storing the vacuum cleaner 200 in a space-saving way while charging its batteries 250, if needed. While in the event of a robotic vacuum cleaner 100, it will typically be the full vacuum cleaner 100 that is docked at the docking station 190, this may be different for non-robotic vacuum cleaners, For the stick vacuum cleaner 200 of FIG. 5, for example, only an element of the vacuum cleaner 200, such as the main body 203 or the cleaner head 201 may be docked. The docking station may further include one or more sources of violet visible light for illuminating specific parts of the vacuum cleaner 200. As for the robotic vacuum cleaner 100 of FIGS. 1 to 4, the control of the decontamination process may be performed by a controller in the docking station, by the controller in the vacuum cleaner 200, or by a combination of both. The docking station may include separate docking bays for the main body 203, the stick 202 and the cleaner head 201. Additional docking bays may be provided for additional attachment pieces. Violet visible light sources may be provided for each separate part that is stored in the docking station. Docking sensors, e.g. contact sensors or optical sensors may be used for detecting when any of the vacuum cleaner parts (including the main body 203) is positioned in its respective docking bay and the decontamination program may include selectively operating only the light sources configured for decontaminating the docked parts.

Figure 6:
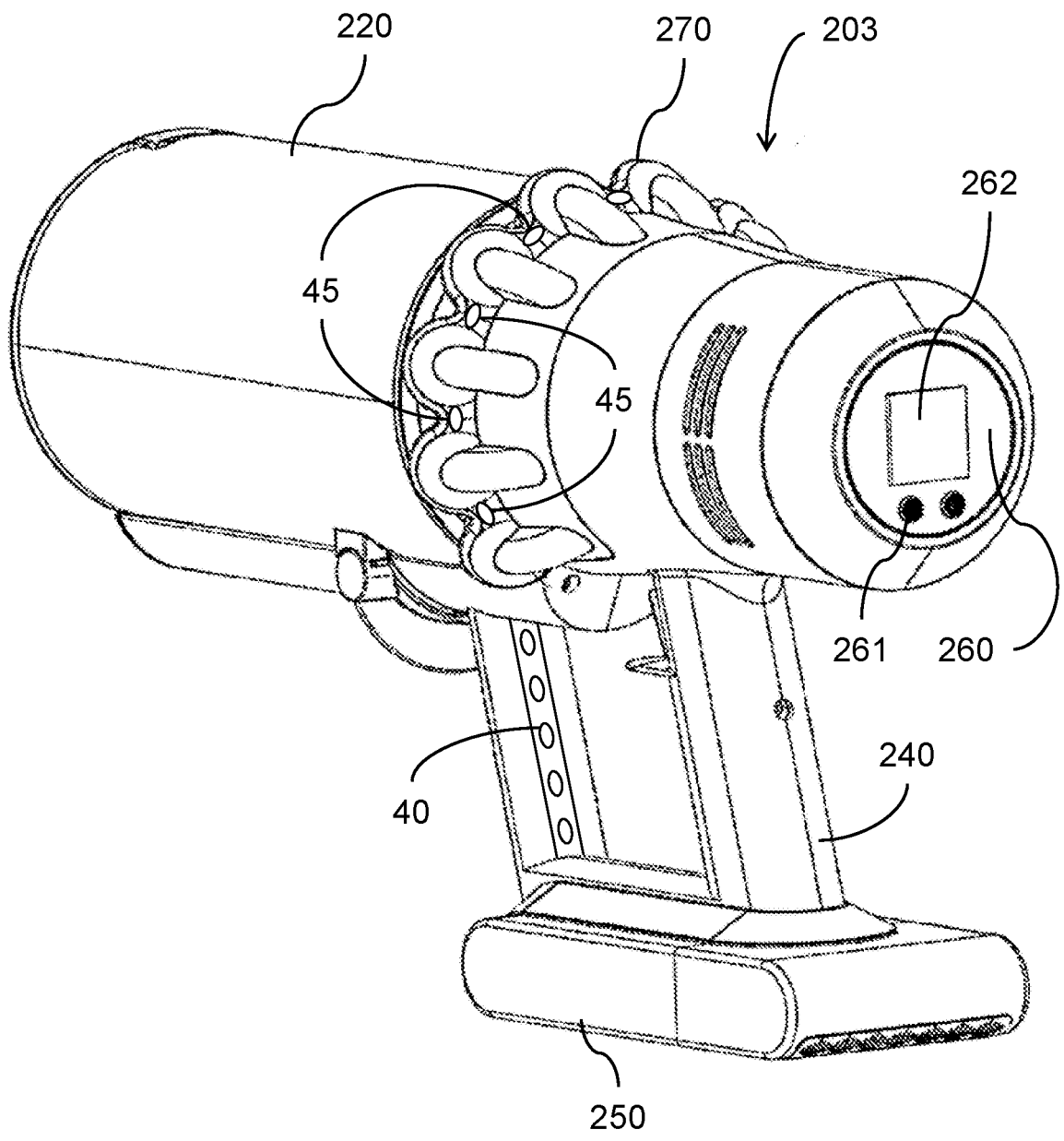
FIG. 6 shows a main body for the stick vacuum cleaner of FIG. 5.

FIG. 6 shows a main body 203 for the stick vacuum cleaner 200 of FIG. 5, in more detail. In addition to the features already discussed above, this main body 203 further comprises a user interface 260 with buttons 261 and a display screen 262, which may be a touch screen for allowing more advanced interaction with the control systems of the vacuum cleaner 200. A user interface 260 will be frequently touched by the user. LED light sources may be integrated in the user interface 260 for decontaminating this often-touched area. For example, LED light sources may be provided in or near the buttons 261. Alternatively, the display screen 262 itself may be configured to emit light in the violet portion of the visual spectrum. Like other visible violet light sources of the vacuum cleaner, the display screen may emit the violet light when the vacuum cleaner 200 is in a park mode, but also during use in the floor care mode.

An LED strip 40 for emitting violet visible light is installed opposite the handle 240 to allow for decontamination of that handle 240. The LED strip 40 may be attached to the handle or, if the handle is made of transparent material, integrated in the handle. Additional LEDs 45 are provided on the main body 203, in between the cones of the cyclonic separator 270. These additional LEDs 45 can illuminate the surface of the main body 203 which, during use, is often touched by users and therefore prone to microbial contamination.

Figure 7:
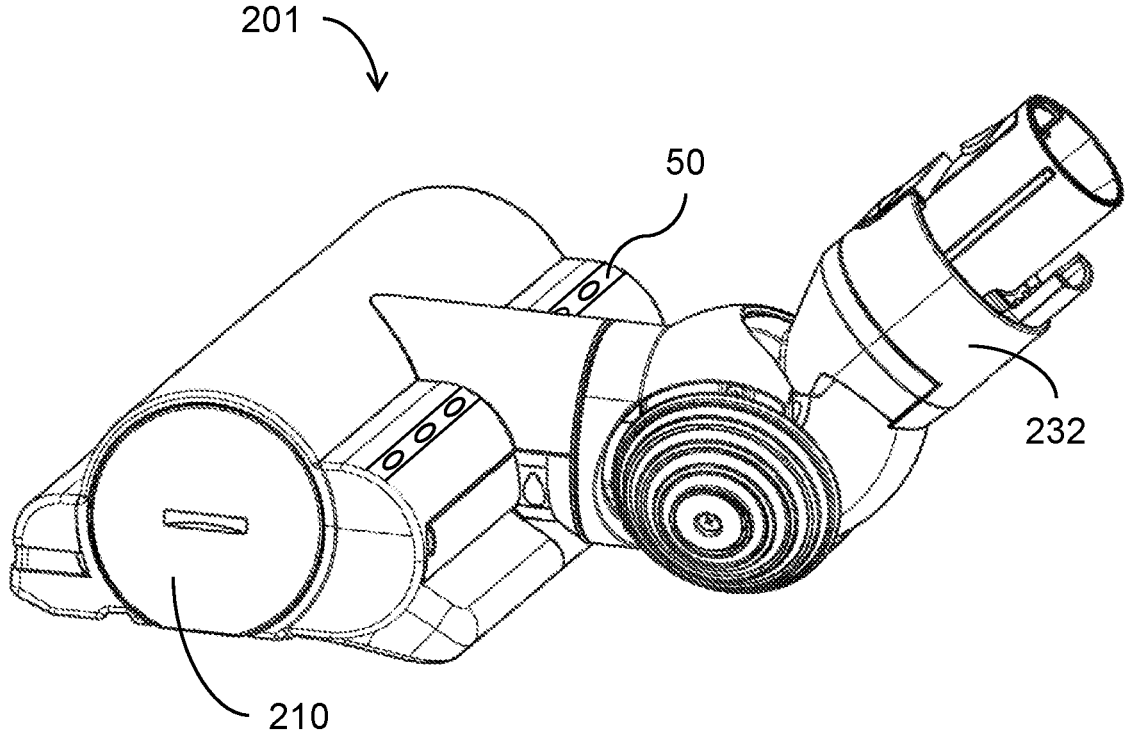
FIG. 7 shows a cleaner head for the stick vacuum cleaner of FIG. 5.

FIG. 7 shows a cleaner head 201 for the stick vacuum cleaner 200 of FIG. 5. A light strip 50 is provided at its top surface for illuminating the stick 200 and the stick connector 232 when the decontamination program is executed.

Figure 8:
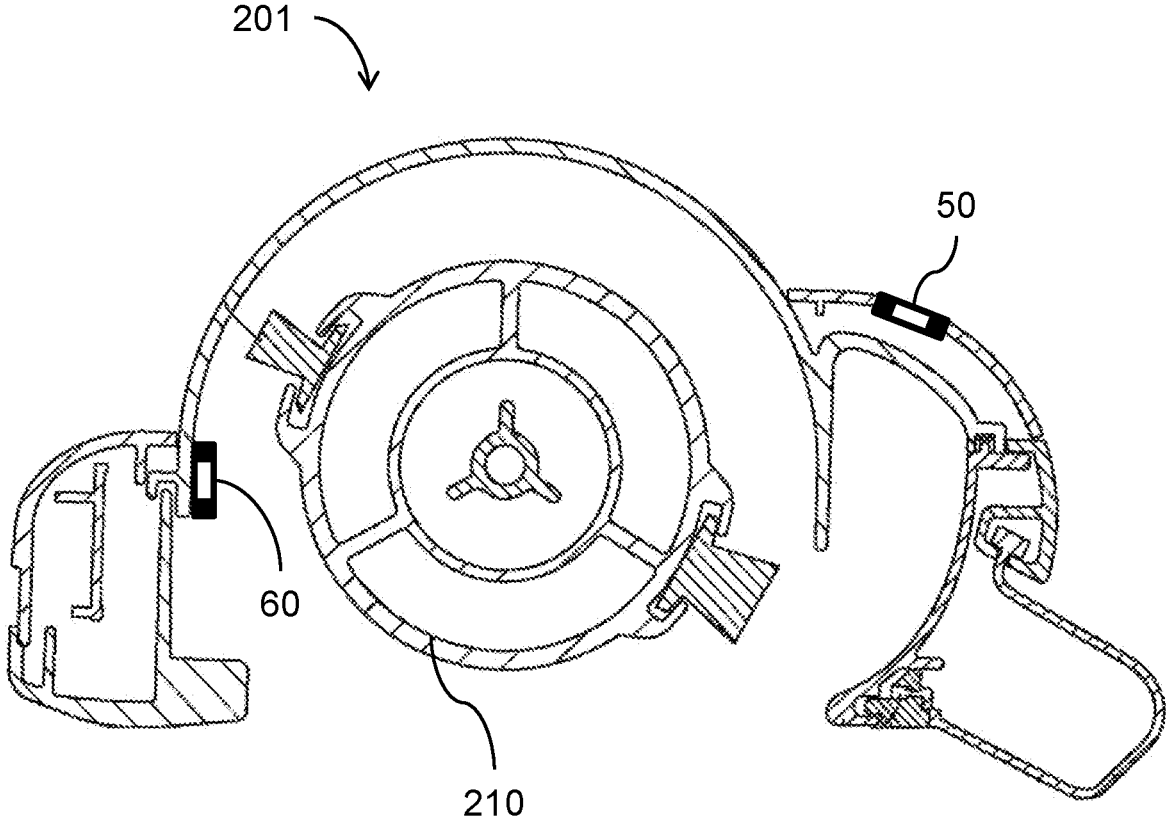
FIG. 8 shows a cross section of the cleaner head of FIG. 7.

FIG. 8 shows a cross section of the cleaner head 201 of FIG. 7. It shows the same light strip 50 as already shown in FIG. 7, plus a further light strip 60. This additional light strip 60 is positioned opposite and in close proximity to the brush bar 210. Since this light strip 60 can only illuminate one side of the brush bar 210, the brush bar 210 is preferably rotated as part of the decontamination program. Alternatively, additional light strips and/or light guides are provided for ensuring that all sides of the brush bar 210 are equally illuminated.

Figure 9A:
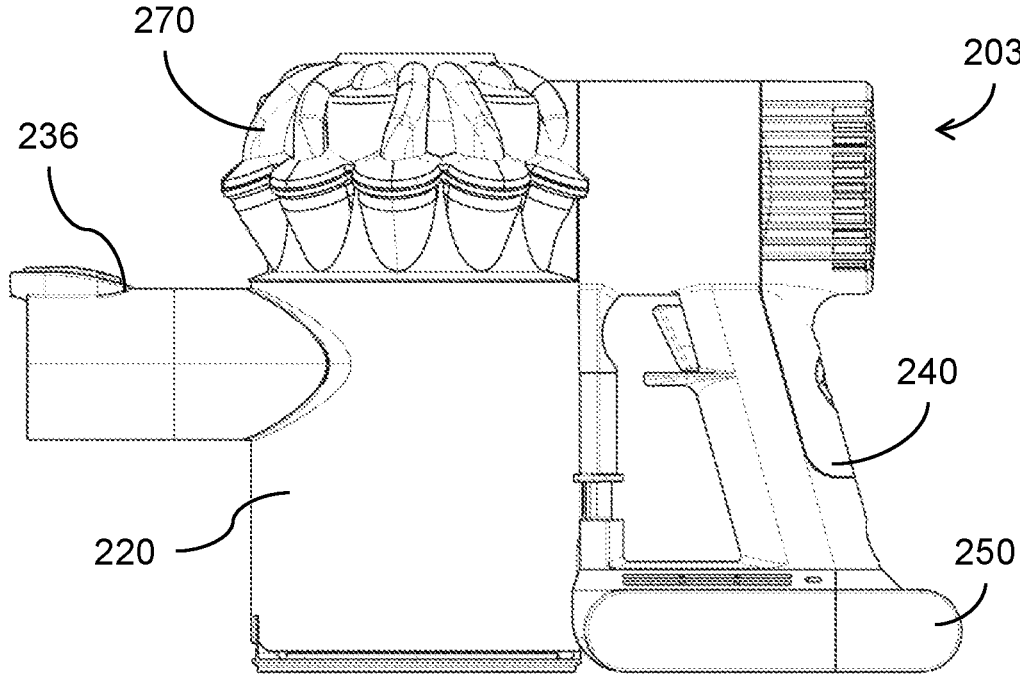
FIG. 9a shows a main body for different vacuum cleaner.
Figure 9B:
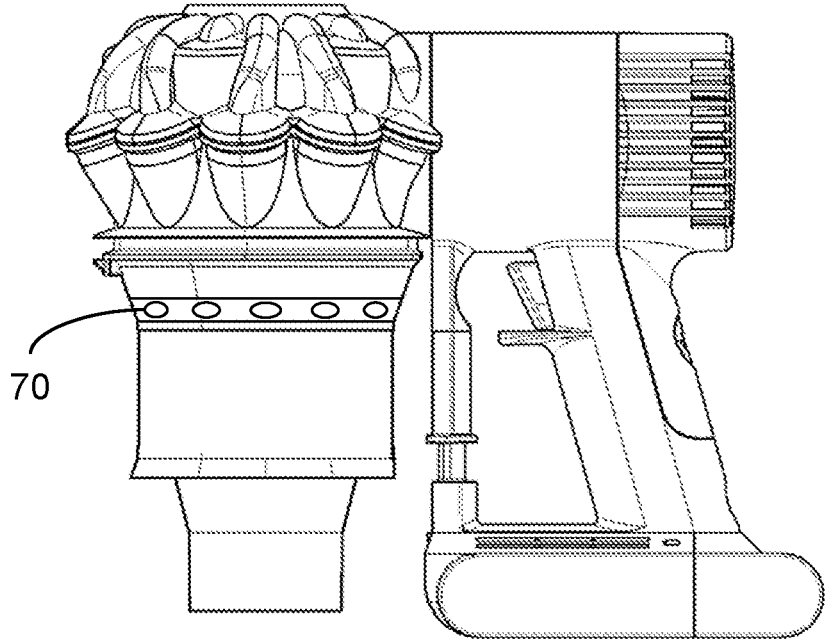
FIG. 9b shows the main body of FIG. 9a with its dust bin removed.

FIG. 9*a* shows a main body 203 for different vacuum cleaner. This main body 203 comprises an attachment connector 236 that is configured for the attachment of a cleaner head or different type of cleaner tool. If connected to a stick, the main body 203 may be used for a stick vacuum cleaner similar to the one shown in FIG. 5. Alternatively, it is used for a compact handheld vacuum cleaner. FIG. 9*b* shows the main body 203 of FIG. 9*a* with its dust bin 220 removed. Removing the dust bin reveals the cyclonic separator 270. A circular light strip 70 is provided around a circumference of the cyclonic separator 270 for illuminating the dust bin 220 from the inside. If the dust bin 220 is made of at least partially transparent material, it may serve as a light guide for illuminating other parts, such as the attachment connector 236 and the handle 240 of the main body 203. Since the circular light strip 70 is positioned close to the top of the dust bin 220, the light is unlikely to be obscured when the dust bin 220 is not emptied before the decontamination program starts.

The invention has been described above in relation to a number of different embodiments. It is to be noted that the invention is equally applicable to other types of vacuum cleaners. Further, features used in and described with reference to specific embodiments are combinable with other embodiments. The scope of the invention is only limited by the following claims.

The invention claimed is:

1. A docking station for a floor care device, the floor care device comprising at least one part that is susceptible to contamination when the floor care device is used in a floor care mode, the docking station comprising:
   a docking bay for receiving and holding at least an element of the floor care device,
   a docking sensor for providing a docking signal when at least the element of the floor care device is held in the docking bay,
   at least one light source for emitting light in a violet portion of the visible spectrum, the violet portion of the visible spectrum defined as light within the wavelength range of 380 nm to 450 nm, the at least one light source being arranged in such a way as to illuminate the at least one part of the floor care device by emitting the light while the floor care device is being held in the docking bay,
   a docking station controller, operatively coupled to the docking sensor and the at least one light source and operative to receive the docking signal and to execute, in response thereto, a decontamination program, the decontamination program including using the at least one light source to illuminate the at least one part of the floor care device for the decontamination thereof, and
   a communication unit, operatively coupled to the docking station controller, for enabling communication between the docking station controller and a floor care controller of the floor care device.

2. The docking station as claimed in claim 1, wherein the at least one light source is configured for emitting light with a wavelength of 405 nm.

3. The docking station as claimed in claim 1, further comprising a contamination detector for detecting contamination on a contaminated portion of the at least one part of the floor care device and wherein the decontamination program comprises selectively illuminating the contaminated portion.

4. The docking station as claimed in claim 1, the decontamination program comprising receiving, from the floor care controller, a contamination signal indicating a contaminated portion of the at least one part, and in response to the contamination signal selectively illuminating the contaminated portion.

5. The docking station as claimed in claim 1, the decontamination program comprising sending, to the floor care controller, an instruction to rotate the at least one part, and illuminating the at least one part during and/or after rotating the at least one part.

6. A combination comprising:
   the docking station as claimed in claim 1 and
   a floor care device, the floor care device comprising at least one part that is susceptible to contamination when the floor care device is used in a floor care mode.

7. The combination as claimed in claim 6, wherein the floor care device further comprises at least a second part that is susceptible to contamination when the floor care device is used in the floor care mode, and wherein, when the floor care device is received in and held by the docking bay, the at least one part is situated between the at least one light source and the second part and configured to guide the light emitted by the light source towards the second part.

8. The combination as claimed in claim 7, wherein the at least one part is a dust bin.

9. The combination as claimed in claim 8, wherein the second part is an air filter, or a shroud for at least partially enclosing the dust bin.

10. The combination as claimed in claim 6, wherein the wherein the floor care device further comprises a floor care controller, and wherein the docking station and the floor care device each comprise a communication unit, operatively coupled to their respective controllers for enabling communication between the docking station controller and a floor care controller of the floor care device.

11. The combination as claimed in claim 10, the decontamination program comprising the docking station controller receiving, from the floor care controller, a contamination signal indicating a contaminated portion of the at least one part, and in response to the contamination signal selectively illuminating the contaminated portion.

12. The combination as claimed in claim 10, wherein the at least one part is a rotatable part, and wherein the decontamination program comprises the docking station controller sending, to the floor care controller, an instruction to rotate the rotatable part, and illuminating the rotatable part during and/or after rotating the rotatable part.

13. A docking station for a floor care device, the floor care device comprising at least one part that is susceptible to contamination when the floor care device is used in a floor care mode, the docking station comprising:
   a docking bay for receiving and holding at least an element of the floor care device,
   a docking sensor for providing a docking signal when at least the element of the floor care device is held in the docking bay,
   at least one light source for emitting light in a violet portion of the visible spectrum, the violet portion of the visible spectrum defined as light within the wavelength range of 380 nm to 450 nm, the at least one light source being arranged in such a way as to illuminate the at least one part of the floor care device by emitting the light while the floor care device is being held in the docking bay,
   a docking station controller, operatively coupled to the docking sensor and the at least one light source and operative to receive the docking signal and to execute, in response thereto, a decontamination program, the decontamination program including using the at least one light source to illuminate the at least one part of the floor care device for the decontamination thereof; and
   a contamination detector for detecting contamination on a contaminated portion of the at least one part of the floor care device and wherein the decontamination program comprises selectively illuminating the contaminated portion.

14. A combination comprising:
   a floor care device, the floor care device comprising at least one part that is susceptible to contamination when the floor care device is used in a floor care mode, wherein the at least one part is a dust bin, and wherein the floor care device further comprises at least a second part that is susceptible to contamination when the floor care device is used in the floor care mode; and
   a docking station for the floor care device, the docking station comprising:
      a docking bay for receiving and holding at least an element of the floor care device,
      a docking sensor for providing a docking signal when at least the element of the floor care device is held in the docking bay, at least one light source for emitting light in a violet portion of the visible spectrum, the violet portion of the visible spectrum defined as light within the wavelength range of 380 nm to 450 nm, the at least one light source being arranged in such a way as to illuminate the at least one part of the floor care device by emitting the light while the floor care device is being held in the docking bay, and a docking station controller, operatively coupled to the docking sensor and the at least one light source and operative to receive the docking signal and to execute, in response thereto, a decontamination program, the decontamination program including using the at least one light source to illuminate the at least one part of the floor care device for the decontamination thereof, wherein, when the floor care device is received in and held by the docking bay, the at least one part is situated between the at least one light source and the second part and configured to guide the light emitted by the light source towards the second part.

* * * * *